United States Patent [19]

Nomura et al.

[11] Patent Number: 5,091,535
[45] Date of Patent: Feb. 25, 1992

[54] ORGANIC PHOTOCHROMIC COMPOUND, A DIMER OF PYRIDO QUINOLINE

[75] Inventors: Shigeru Nomura; Takahiro Hidaka, both of Tsukuba, Japan

[73] Assignee: Seikisui Kagaku Kogyo Kabushiki Kaisha, Japan

[21] Appl. No.: 513,637

[22] Filed: Apr. 24, 1990

[30] Foreign Application Priority Data

Apr. 27, 1989 [JP] Japan .................................. 1-110421
Feb. 22, 1990 [JP] Japan .................................. 2-42023

[51] Int. Cl.$^5$ .................. C07D 471/22; C07D 471/04; G03C 1/73
[52] U.S. Cl. ........................................ 546/35; 546/81; 430/343; 430/962; 204/157.71
[58] Field of Search .................. 546/81, 35; 430/343, 430/962; 204/157.46, 157.71, 157.72

[56] References Cited

U.S. PATENT DOCUMENTS 2,650,225  8/1953  Goldberg et al. .................... 546/81
4,061,638 12/1977  Brown et al. ......................... 546/81

Primary Examiner—Charles L. Bowers, Jr.
Assistant Examiner—John S. Y. Chu
Attorney, Agent, or Firm—Dykema Gossett

[57] ABSTRACT

An organic photochromic compound with improved long term preservability, thermal stability, the repetition character of the record and the like and useful as recording-memory materials or photosensitizers, comprising dimers of the compounds selected from the group consisting of pyrido[3,4-g]isoquinoline, pyrido[2,3-g]quinoline, pyrido[3,2-g]quinoline and pyrido[3,2-g]quinoline derivatives.

1 Claim, 1 Drawing Sheet

ORGANIC PHOTOCHROMIC COMPOUND, A DIMER OF PYRIDO QUINOLINE

BACKGROUND OF THE INVENTION

1. Field of the Invention

This invention relates to organic photochromic compounds which show photochromism and which are useful as various recording-memory materials or photosensitizers.

2. Description of the Prior Art

A photochromic compound is a compound which shows coloring and discoloring i.e. a "memory" material with reversible photoresponsivity.

The reversible structural changes of photochromic compounds owing to tautomerization, trans-cis isomerization, cyclization, dimerization, ionic dissociation may occur by photoirradiation and also by change of absorption spectrum simultaneously. Since these phenomena (photochromism) are due to changes at the molecular level, the photochromic compound is known as memory material with ultra-high denisty. For example, an expected application is reversible bit-recording material for photodisc, photosensitive material for holograms, or laser recording material. Additionally, owing to its remarkable color changing property the photochromic material with rapid reversible responsivity reaction may be used as an indicator material.

Many inorganic and organic compounds demonstrate photochromism, but in addition to advantages they have problems also.

That is, inorganic photochromic compounds such as $Hg_3S_2I_2$ or $ZnS$ and the like lack workability, abundance of color, and humidity resistance.

On the other hand, various organic photochromic compounds such as azobenzene, spiropyran, viologen, spironaphtooxazine, anthracene, fulgide, stilbene and the like and their derivatives are known. For example, spironaphtohooxazine derivatives and spirobenzopyran are disclosed as photochromic compound in Japanese Patent Publication Nos. 28892/1970, 48631/1974 and Japanese Unexamined Patent Publication No. 36284/1980.

In general, the organic photochromic compound has many advantages such as good workability, the ability of molecular modification to its derivatives to meet to an object, and of formation of various media by dispersion to macromolecular film or covalent crystallization or direct vacuum evaporation to macromolecule, as is desirable of photomemory materials.

However, these known organic photochromic compounds have problems with regard to long term preservability of coloration condition, thermal stability, the repetition character of record (the property relating to the ability of reversible and stable regeneration of record) and the like; thus for this reason they are not used widely now as recording-memory material.

SUMMARY OF THE INVENTION

The object of the present invention is to provide organic photochromic compounds with excellent properties with respect to long term preservability of coloration condition, thermal stability, the repetition stability of reversible reaction, quantum yield of photoreaction and the like.

The present inventors continued studies earnestly to overcome said problems of the prior art, and found that a compound which is selected from the group consisting of pyrido[3,4-g] isoquinoline, pyrido[2,3-g]quinoline, pyrido[3,2-g] quinoline and pyrido[3,2-g] quinoline derivatives showed photochromism in that they produce a dimer irradiated with UV-radiation of a wavelength of from about 320 to 400 nm, and by reverting to the original compounds when said dimer was irradiated with UV-radiation of a wavelength of from about 230 to 300 nm.

In addition, the present inventors discovered that said dimer was a suitable compound as a memory material because of its excellent thermal stability, e.g. even under the heating condition of 80 degrees for 20 days, it did not revert to the original compound and recording condition was maintained.

The present invention was accomplished on these findings.

According to the present invention, there is provided an organic photochromic compound comprising a compound selected from the group consisting of pyrido[3,4-g]isoquinoline of chemical formula [I]

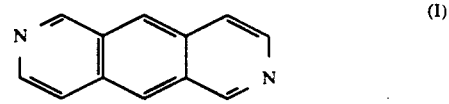

pyrido[2,3-g]quinoline of chemical formula [II]

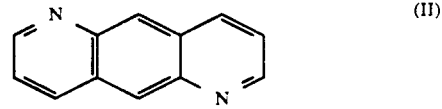

pyrido[3,2-g]quinoline of chemical formula [III]

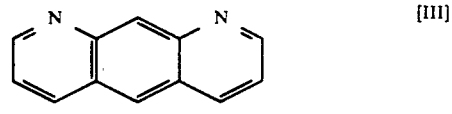

and pyrido[3,2-g]quinoline derivatives of chemical formula [IV]

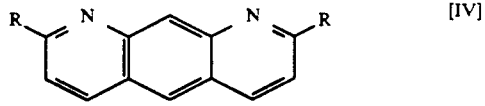

wherein R is methyl, ethyl, propyl, butyl, carboxy, carboxymethyl, or carboxyethyl.

This invention will hereinafter be described in detail.

(Pyrido[3,4-g]isoquinoine)

Pyrido[3,4-g]isoquinoline is known compound, and may be prepared as follows:

5,10-dioxy-pyrido[3,4-g]isoquinoline is synthesized by reacting N,N-diethylnicotineamide under the presence of lithium diisopropylamide (LDA) and hexamethylphosphoric triamine (HMPT) in inert gas atmosphere at −78° C. The 5,10-dioxy-pyrido [3,4-g]isoquinoline is reduced to 5,10-dihydro-pyrido[3,4-g]isoquinoline by hydrogen iodide (HI). The objective, pyrido[3,4-g]isoquinoline, is obtained by the treatment of the 5,10-dihydoro-pyrido[3,4-g]isoquinoline with palladium-on-charcoal.

The above synthetic reaction may be represented by following sequence:

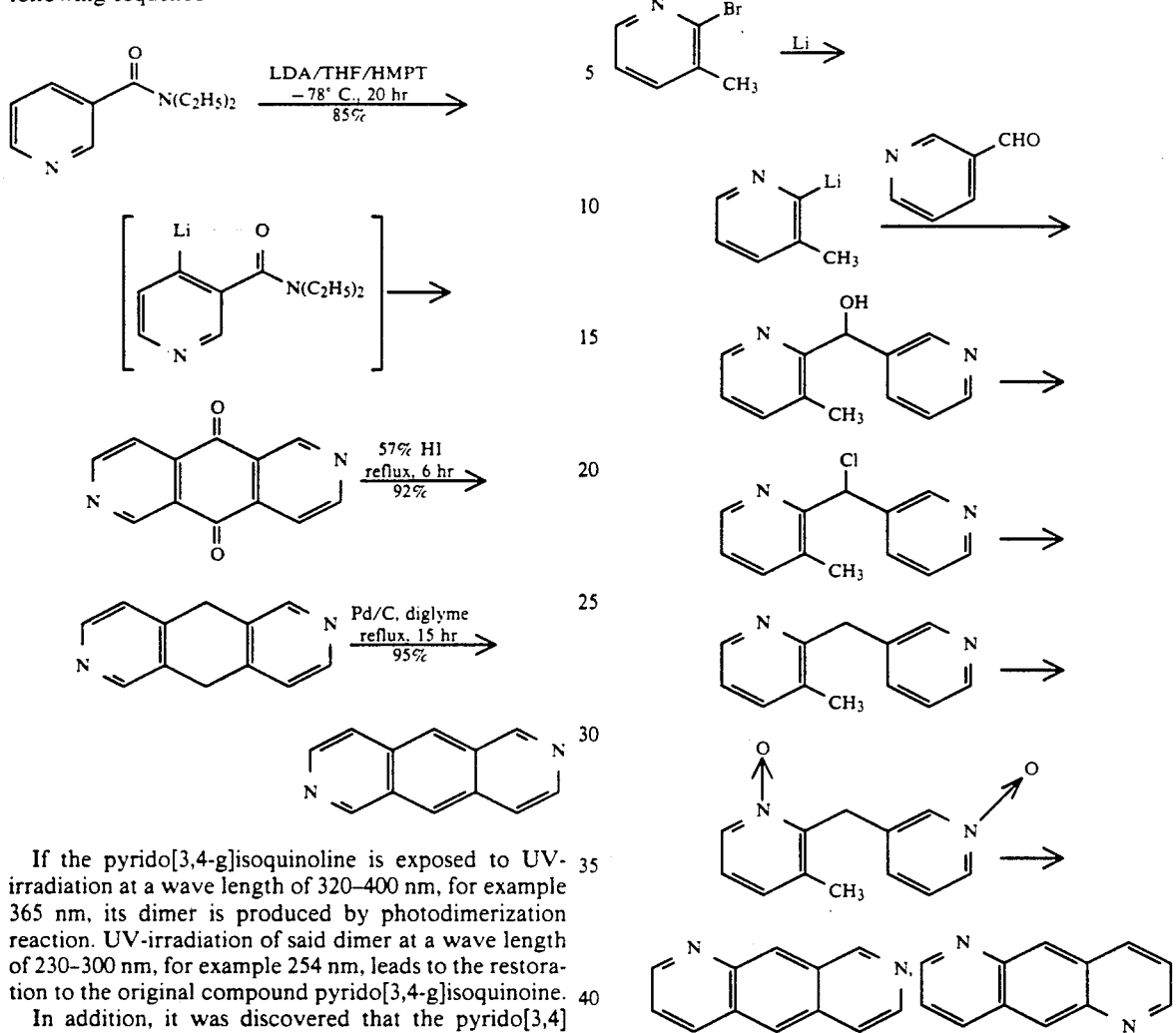

If the pyrido[3,4-g]isoquinoline is exposed to UV-irradiation at a wave length of 320–400 nm, for example 365 nm, its dimer is produced by photodimerization reaction. UV-irradiation of said dimer at a wave length of 230–300 nm, for example 254 nm, leads to the restoration to the original compound pyrido[3,4-g]isoquinoine.

In addition, it was discovered that the pyrido[3,4]isoquinoline was also restored from the original dimer by heating at a temperature above 120° C. in an appropriate solvent. This dimer is stable and is suitable for memory material because it does not revert to the original compound at a temperature under 120° C.

The photodimerization reaction may be represented by following sequence:

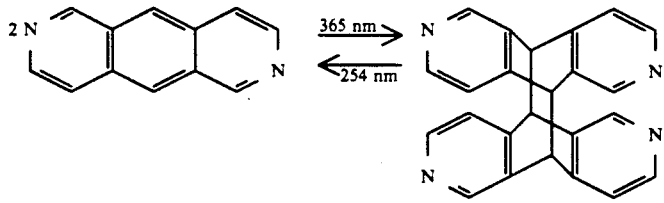

(Pyrido[2,3-g]quinoline)

Pyrido[2,3-g]quinoline is known compound, and may be synthesized by following sequence:

Namely, the synthesis of the objective compound may be accomplished by carrying out successively following steps: 1) the synthesis of 3-methyl-2-lithiopyridine by reacting starting material 2-bromo-3-methylpyridine with lithium, 2) the synthesis of 3-pyridyl-2-(3-methylpyridyl)methanol by reacting the 3-methyl-2-lithiopyridine with pyridine-3-aldehyde, 3) the synthesis of 3-pyridyl-2-(3-methylpyridyl) chroromethane by reacting the 3-pyridyl-2-(3-methylpyridyl)methanol with thionyl chloride, 4) the synthesis of 3-pyridyl-2-(3-methylpyridyl) methane from 3-pyridyl-2-(3-methylpyridyl)chroromethane, 5) the synthesis of 3-pyridyl-2-(3-methylpyridyl)methaneoxide from 3-pyridyl-2-(3- methylpyridyl)methane, 6) the synthesis of pyrido[2,3-g]quinoline by subjecting the 3-pyridyl-2-(3-methyl-pyridyl)methaneoxide to flash vacuum pyrolysis(FVP).

Although pyrido[4,3-g]quinoline is contained in the reaction product of FVP process, it can be separated from pyrido[2,3-g]quinoline by liquid chromatography.

(Pyrido[3,2-g]quinoline)

Pyrido[3,2-g]quinoline is known compound, and may be synthesized by following sequence which is disclosed, for example, in Liebigs Ann. Chem., 1984, pp. 133-146.

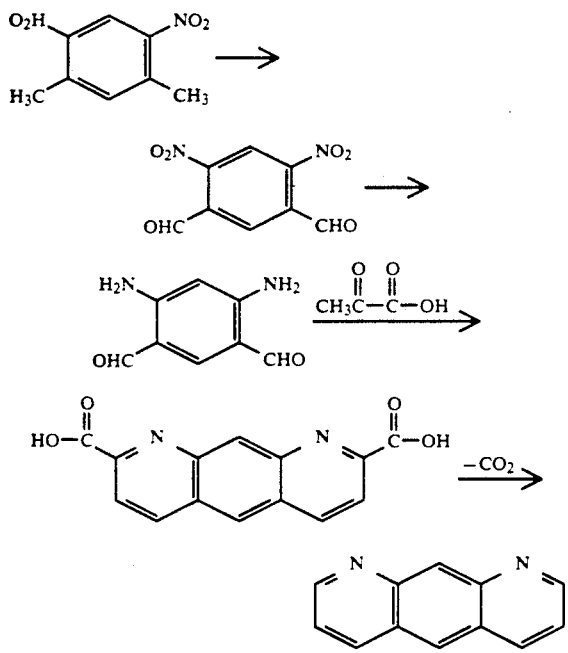

If the pyrido[3,2-g]quinoline is exposed to UV-irradiation at a wavelength of 320–400 nm, for example 365 nm, its dimer is produced by photodimerization reaction. UV-irradiation of said dimer at a wavelength of 230–300 nm, for example 254 nm, leads to the restoration to the original compound pyrido [3,2-g]quinoline.

The photodimerization reaction may be represented by following sequence:

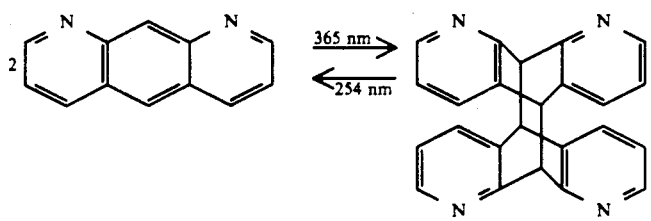

(Pyrido[3,2-g]quinoline derivatives)

Pyrido[3,2-g]quinoine derivatives are known compounds, and may be synthesized, for example, by following sequence:

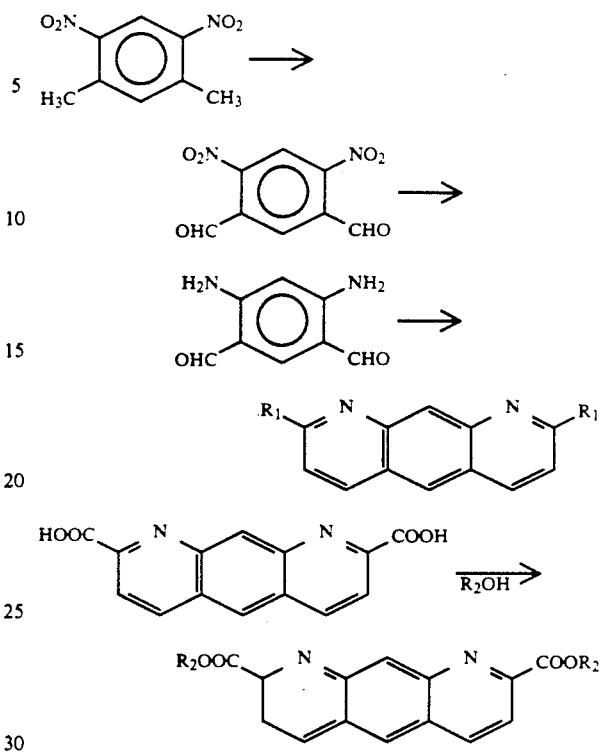

Namely, the 4,6-diaminoisophthalaidehyde which is obtained from above-described synthetic reaction of pyrido[3,2-g]quinoline is allowed to react, for example, with acetone to form 2,8-dimethyl pyrido[3,2-g] quinoine ($R_1$; —$CH_3$) or with 3,3-dimethylbutane-2-on to form 2,8-di-terbutylpirido [3,2-g]quinoline[$R_1$; —$C(CH_3)_3$]. Additionally, the reaction of pyrido[3,2-g]quinoline-2,8-dicarboxylic acid from said synthetic reaction of pyrido[3,2-g]quinoline with methyl alcohol results in esterification to form dimethyl pyrido [3,2]quinoline-2, 8-dicarboxylate.

The synthetic process of these compounds are disclosed in Liebigs Ann. Chem., 1984, pp. 133-146.

If these compounds are exposed to UV-irradiation at a wavelength of 320–400 nm, for example 365 nm, their dimers are produced by photodimerization reaction. UV-irradiation of said dimers at a wavelength of 230–300 nm, for example 254 nm, leads to the restoration to the original compound. The photodimerization reactions may be represented respectively by above-described sequences.

Thus, with respect to each of pyrido[3,4-g]isoquinoline, pyrido[2,3-g]quinoline, pyrido[3,2-g]quinoline, and pyrido[3,2-g] quinoline derivatives, it was proved that reversible photodimerization reaction of the compounds may occur, and that they therefore demonstrate photochromism.

In these dimers, decomposition was not observed nor any changes in absorbance even after 20 days at 80° C., and they proved to be excellent in thermal stability. These dimers after heat treatment were also shown to be restored to original compound photoirradiation of wavelength 254 nm.

In addition, the dimers of these compounds may also be restored to the original compound by heating at a temperature above 160° C. in solution. But in the solid state, they may not be restored to the original compound even under heating at 160° C., and are reactive by light reversibly.

It may be realized from above-described experimental results that these compounds are organic photochromic compounds with excellent properties with respect to long term preservability, thermal stability, the repetition character of record and the like and are useful as recording-memory material.

Figure 1:
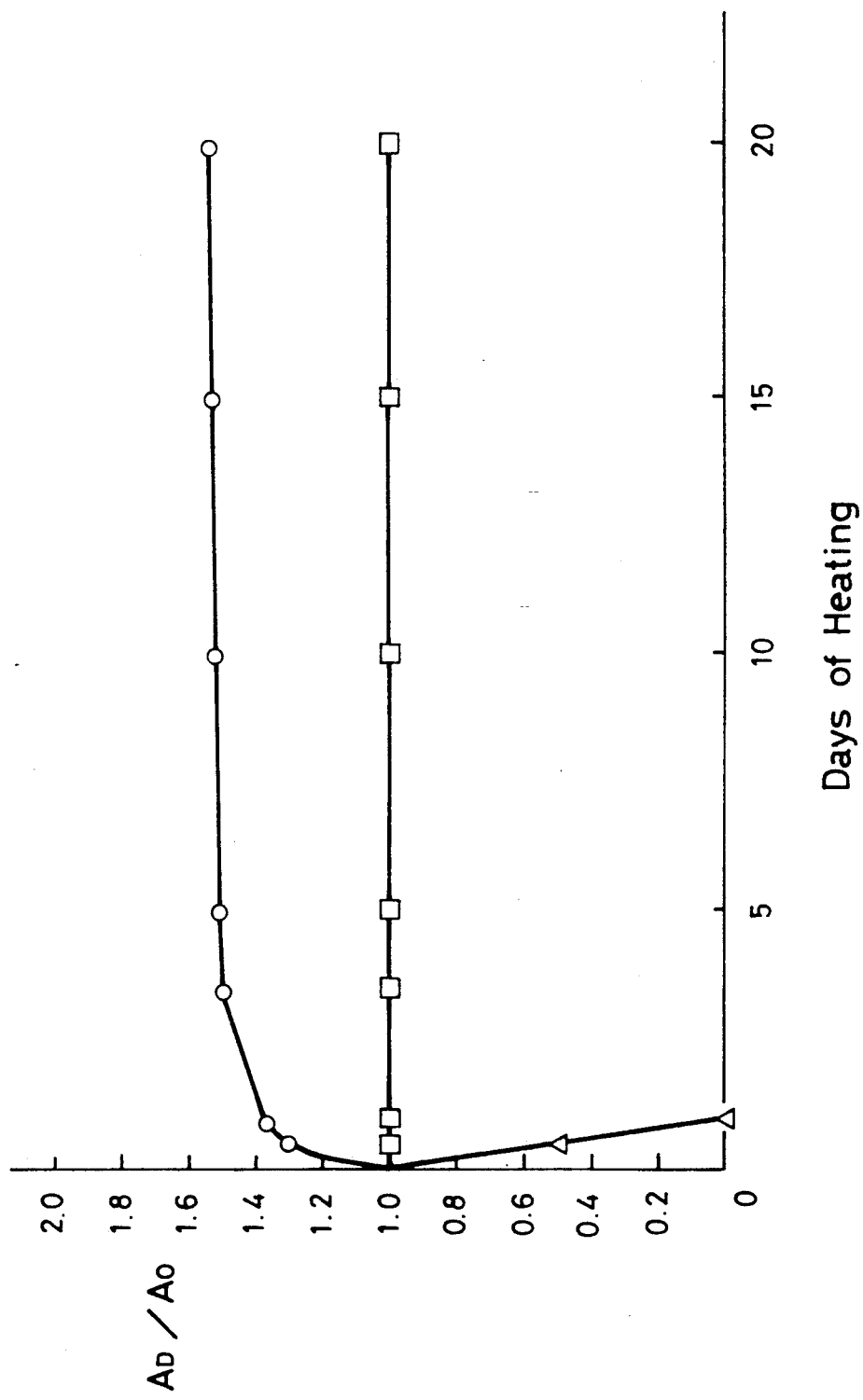
FIG. 1 shows the changes of the absorbance of the coloring form of the following three organic photochromic compounds under the heating condition (in air, heating by oven) at 80° C.

□: dimer of pyrido[2,3-g]quinoline
o: dimer of anthracene
Δ: cyclization product of fulgide The change of the absorbance was indicated as $A_D/A_O$, wherein $A_O$ is the absorbance at 365 nm before the heating test and $A_D$ is the absorbance at 365 nm after the heating test (term of heating test: D days).

DETAILED DESCRIPTION OF PREFERRED EMBODIMENTS

This invention will be described particularly by following examples and comparative studies:

EXAMPLE 1

(Pyrido[3,4-g]isoquinoline)

5.4 g of hexamethylphosphoric triamine and 6.1 g of lithium diisopropylamide were dissolved in 70 cc of tetrahydrofuran (THF). To this solution with stirring which was cooled to −78° C., a solution of 3.4 g of N,N-diethylnicotineamide in 5 cc of THF was added dropwise under an argon atmosphere. The temperature of reaction mixture was allowed to elevate gradually to room temperature over 20 hours. After quencing by 100 cc of water followed 3 times extraction with ethyl ether and 2 times extraction with dichloromethane, crude 5,10-dioxy-pyrido [3,4-g]isoquinoline was obtained.

This product was isolated and purified on silica gel chromatography (R-055-15, S15SIL, YMC Ltd.) by employing CH₂Cl₂/Et₂O as a developing solvent.

The yield of the compound was 3.4 g (85%) and its m.p. was 237° C.-238° C. The compound was identified as 5,10-dioxy-pyrido[3,4-g] isoquinoline based upon the following elemental analysis.

Elemental Analysis:
Calculated: C: 68.57, H: 2.88, N: 13.33. Found: C: 68:72, H: 2.88, N: 13:20.

2 g of said 5,10-dioxy-pyrido[3,4-g]isoquinoline was heated with 40 cc of 57% aqueous hydrogen iodide and finished the reaction after reflux of 6 hours. A solution of 292 g of sodium hydrogen sulfite dissolved in 300 cc of ice water was added and pH was adjusted to 8.5 by 2N sodium hydroxide. After the extraction of reaction mixture with dichloromethane, crude 5,10-dihydro[3,4-g]isoquinoline was obtained. The yield was 1.6 g (92%).

1.6 g of 5,10-dihydro-pyrido[3,4-g]isoquinoline and 0.32 g of palladium-on-charcoal was dispersed and mixed in 100 cc of dimethoxyethyl ether, and refluxed for 15 hours under argon atmosphere. After the filtration of palladium-on-charcoal and solvent was evaporated to obtain crude pyrido[3,4-g]isoquinoline. The product was purified by preparative liquid chromatography (gel; R-055-15, S16SIL, YMC Ltd., developing solvent; ethyl alcohol/benzene=3/7). The yield of the compound was 1.3 g (95%) and its m.p. was 174° C. The compound was identified as pyrido [3,4-g]isoquinoline based upon the following elemental analysis.

Elemental Analysis: Calculated: C: 79.97, H: 4.47, N: 15.55. Found: C: 79.87, H: 4.43, N: 15.63.

After the absorbance of the pyrido[3,4-g]isoquinoline which was obtained from above-described process and dissolved in dimethylformamide was determined by spectrophotometer, it was confirmed that said absorbance disappeared by UV-irradiation at 365 nm and reappeared at former 365 nm by UV-irradiation at 254 nm, therefore this reaction might be reversible.

In addition, it was confirmed that the dimer which was produced from monomer by UV-irradiation at 365 nm at first was restored to original pyrido[3,4-g]isoquinoline by heating at 160° C. However, it was also confirmed that this reaction product was not restored to the original compound by heating at 100° C. for 1 hour and has not decomposed by heating at 80° C. for 20 days; therefore, said reaction was rather thermostable.

The fact that the restoration of the photoreaction product to the original compound by irradiation at a wavelength of UV-radiation shorter than in initial irradiation proves that the said product is a dimer.

EXAMPLE 2

(Pyrido[2,3-g]quinoline)

(i) Synthesis of 3-methyl-2-lithiopyridine n-butyl bromide (82,5 g, 0.6 mol) was dissolved to ethyl ether (120 cc) in three-necked flask under argon atmosphere, and then to this reaction mixture while maintaining at 0° C., Li wire(8.5 g, 1.2 mol) dispersed in ethyl ether (300 cc) was added.

After maintaining this condition for 1 hour, the temperature of reaction mixture was cooled to −80° C., and then a solution of 2-bromo-3-methylpyridine (68.8 g, 0.4 mol) in ethyl ether (120 cc) was added dropwise over an additional 30 minutes.

In the reaction mixture with the metallic luster of excess Li powder and the presence of suspended matter, the reaction was considered to have completed when excess Li wire was substantially exhausted.

(ii) Synthesis of 3-pyridyl-2-(3-methylpyridyl)methanol

To the above-described reaction mixture maintained at −80° C., a solution of pyridine-3-aldehyde (42.8 g, 0.4 mol) in ethyl ether (120 cc) was added dropwise, and then maintained at same temperature for 2 hours followed by gradual elevation to room temperature. The reaction was finished after reflux for additional 1 hour.

Water (200 cc) followed by 35% hydrochloric acid (200 cc) was added to treat the yet unreacted material. After the extraction with ethyl ether (300 cc) for three times, the water layer was neutralized by sodium hydroxide. The water layer was extracted with ethyl ether additionally. and the ethyl ether layer was combined and concentrated. After evaporation under reduced pressure, the objective, 3-pyridyl-2-(3-methylpyridyl)-methanol, was obtained.

The b.p. was 156° C. at 1.8 mmHg and the yield was 54%.

(iii) Synthesis of 3-pyridyl-2-(3-methylpyridyl)methane

A solution of thionyl chloride (28 g, 0.25 mol) in benzene (100 g) was added to a solution of 3-pyridyl-2-(3-methylpyridyl)methanol (40 g) in benzene (500 g) while maintaining the temperature of the reaction mixture at 10° C. and stirred vigorously.

A precipitation occurred at first and liquid became viscous gradually. Then the temperature was allowed to elevate to 40° C., and maintained at same. After water was added and alkalized by sodium hydroxide, it was extracted with chloroform three times. The 3-pyridyl-2-(3-methylpyridyl) chloromoethane thus obtained was thermally-unstable and could not be isolated by recrystallization, so crude product was used in the next step directly.

To the crude 3-pyridyl-2-(3-methylpyridyl)-chloromethane (38.5 g) dissolved in acetic acid, zinc powder (31 g) was added at ambient temperature. After the reaction mixture was heated on water bath for 6 hours, the zinc powder was removed and concentrated to a liquid volume ½ and alkalized by sodium hydroxide. Chloroform extraction (3×200 c) gave 3-pyridyl-2-(3-methyl-pyridyl)methane. The product was purified by distillation under reduced pressure.

The yield was 21.2 g (55%).

(iv) Synthesis of Pyrido[2,3-g]quinoline 3-pyridyl-2-(3-methylpyridyl)methae (4 g) and 4-chloro-benzoic acid (4 g) was dissolved in chloroform (300 cc) and reacted in the absence of light for 12 hours and neutralized with aqueous sodium hydroxide and extracted with chloroform (3×100 cc).

The 3-pyridyl-2-(3-methyl-pyridyl)methaneoxide (4 g) thus obtained was subjected to flash vacuum pyrolysis (FVP) at 1100° C., 0.05 mmHg.

The product was subjected to liquid chromatography on silica gel column using ethyl alcohol/hexane (8/2) as eluting agent and UV-detector at 254 nm to yield pyrido[2,3-g]quinoline (1.2 g).

Elemental Analysis: Calculated: C: 79.98, H: 4.47, N: 15.55. Found: C: 79.86, H: 4.55, N: 15.63.

The m.p. was 241°-242.5° C.

After the pyrido[2,3-g]quinoline (3 mg) from the above process was dissolved in cyclohexanol (20 g) and its absorbance was determined by spectrophotometer (Model U-3400, Hitachi Seisakusho, Ltd.), it was irradiated by spectroirradiater (CRM-FA, Nippon Bunkousha, Ltd.,) at a wavelength near 365 nm for 10 minutes. The change of absorbance was recorded and subsequently carried out heating test at 80° C. The results are shown in FIG. 1 using mark □.

As seen in FIG. 1, there was no change in the absorbance of the dimer of pyrido[2,3-g]quinoline of the present invention even under the heating condition at 80° C. for 20 days.

In addition, even this sample was irradiated with mercury lamp at 254 nm after heating test, the dimer was restored to original pyrido [2,3-g]quinoline accompanying with the reversion of the absorbance to the position before irradiation at 365 nm.

For comparison, the same heating test was carried out with the representative photochromic compound, anthracene (production of dimer by UV-irradiation) and fulgide (production of cyclization product by UV-irradiation), the results of which are shown in FIG. 1 using mark ○ for anthracene and mark Δ for fulgide.

The heating test showed that the absorbance of anthracene changed more than 50% against to initial value, and in fulgide coloring form changed substantially to colorless in about 15 hours.

In the case of other photochromic compounds such as spiropyran and spironaphthooxazie, merocyanine compounds which are coloring forms of the aforementioned compounds, these were very unstable and were restored substantially to original compounds after 3 hours at 25° C.

EXAMPLE 3

(Pyrido[3,2-g]quinolene)

(i) Synthesis of 4,6-dinitroisophthalaldehyde 1,3-dimethyl-4, 6-dinitrobenzene (118 g, 0.602 mol) followed by iodine dispersed in dried pyridine (500 cc) was added to dried pyridine (500 cc) in the absence of light under nitrogen atmosphere.

After stirring this mixture for 16 hours at 95° C., resulted brown crystal was removed by filtration and dispersed in ethyl alcohol (2×300 cc) and in ethyl alcohol/ether (cc/cc) solution 1×300 cc), dried by aspiration each time and washed with ether finally to yield 1,1-(4,6-dinitro-1,3-phenylenedimethylene)bis(-pyridinium) diiodie (crude product, 208 g). The yield was 57%.

The crude product from the above process (121 g) and 4-nitroso-N,N-dimethylaniline hydrogen chloride (82 g, 0.44 mol) were added to ethyl alcohol (1.2 cc), and to the mixture with stirring strongly at 5° C., 10% sodium hydroxide (350 cc) was added dropwise over 30 minutes. The mixture was further stirred for 7 hours at 5° C. and allowed to stand for 14 hours at room temperature. The resultant deep red crystal was removed by filtration and dispersed in water (3×1 cc) and ethyl alcohol/ether (cc/cc) solution (1×300 cc), dried by aspiration each time and washed with ether (200 cc) finally to yield N,N-(4,6-dinitro-1,3-phenylenedimethylidyne)bis(N,N-dimethyl-1,4-phenylenediamine)-N,N-dioxide (76 g).

To a solution of the compound (37.5 g, 80 mmol) from the above process in toluene (600 cc), 6N hydrochloric acid (300 cc) was added gradually at 65° C. under nitrogen atmosphere. After 3 hours the toluene layer was separated and fresh toluene (500 cc) was added to the water layer and stirred for 3 hours at 65° C. The toluene layer thus obtained and of the former was combined and washed with water (500 cc) and evaporated to yield 4,6-dinitroisophthalaldehyde. The yield was 10.7 g.

(ii) Synthesis of 4,6-diaminoisophthalaldehyde

To a solution (400 cc) of ferrous sulfate (II) 5 hydrate (184 g 0.65 mol), stirring well, was added equimolar of conc. sulfuric acid. Then a solution of 4,6-diaminoisophthalaldehyde (8.0 g, 35 mmol) in warm ethyl alcohol (300 cc) was added dropwise, and then added conc. acqueous ammonia (180 cc) was added. After the reaction mixture was stirred for 1 hour at 80° C., the precipitate was recrystallized from a solution of water/alcohol (5/1) to yield a brown solid, the yield of which was 2.10 g.

(iii) Synthesis of Pyrido [3,2-g]quinoline-2,8-dicarboxylic acid

To 4,6-diaminoisophthalaldehyde (1,64 g) and 2-oxopropionic acid (1.94 g), ethyl alcohol (40 cc) was added and 2N sodium hydroxide solution (12.8 cc) was added with stirring at 80° C. and allowed to react for 4 hours. Then, 2-oxopropionic acid (0.41 g) and 2N sodium hydroxide solution (3 cc) were added and refluxed for 2 hours. After the addition of 2N aqueous ammonia (50 cc) and water (130 cc) and heating and filtration, charcoal was added with stirring. Refiltration and pH adjustment to 4-5 by 0.6N hydrochloric acid and 0.3N acetic acid a5 70°-80° C. gave solid which is hard to dissolve.

(iv) Synthesis of Pyrido[3,2-g]quinoline

Diethylene glycol monomethyl ether (20 cc) was added to pyrido[3,2-g] quinoline-2,8-dicarboxylic acid (2.01 g, 7.5 mmol) from the above process and cuprous oxide (I) (50 mg, 0.35 mmol), and heated for 5.5 hours at 165° C. Carbon dioxide evolved during the reaction. After the addition of conc. aquous ammonia (25 cc), extracted with dichloromethane (3×100 ml) and dried on potassium carbonate and evaporated dichloromethane to yield pyrido[3,2-g]quinoline.

Elemental Analysis: Calculated: C: 79.98, H: 4;47, N: 15.55. Found: C: 79.86, H: 4.38, N: 15.76.

The m.p. was 164.5°-165.5° C.

After the pyrido[3,2-g]quinoline (3 mg) from the above process was dissolved in cyclohexanol (20 g) and its absorbance determined by spectrophotometer, it was irradiated by UV-radiation from a spectroirradiator at a wavelength near 365 nm for 10 minutes. After the change of absorbance was recorded, a heating test was carried out at 80° C. The absorbance of the dimer of pyrido[3,2-g] quinoline of the present invention was not changed even under the heating condition of 80° C., 20 days. This result was same as that of the dimer of pyrido[2,3-g]quinoline showed in FIG. 1.

In addition, when this sample was irradiated by a mercury lamp at 254 nm after the heating test, the dimer was restored to the original pyrido[3,2-g]quinoline accompanied by the reversion of the absorbance to the position before irradiation at 365 nm.

EXAMPLE 4

(2,8-dimethylpyrido [3,2-g]quinoline)

To 4,6-diaminoisophthalaldehyde (0.82 g) which as prepared in the same manner as Example 3, acetone (8.7 g) was added and the temperature of resulted solution elevated to 56 C. To this solution, 10% potassium hydroxide/ethyl alcohol solution (1.0 cc) was added dropwise and stirred for 45 minutes.

After the end of the reaction, excess acetone was evaporated and 2N hydrochloric acid (100 cc) was added. After the extraction with diethyl ether (3×20 cc), it was neutralized with saturated sodium hydrogen carbonate solution and extracted with dichloromethane (3×30 cc). The solution was dried on anhydrous sodium sulfate and extracted with solvent to yeld yellow crystals.

Elemental Analysis: Calculated: C: 80.72, H: 5.82, N: 13.58. Found: C: 80.65, H: 5.86, N: 13.49.

After, 2,8-dimethylpyrido[3,2-g]quinoline (3 mg)] from above process was dissolved in cyclohexanol (20 g) and its absorbance determined by spectrophotometer, it was irradiated by UV-radiation from a spectroirradiator at a wavelength near 365 nm for 10 minutes. After the change of the absorbance was recorded, and a heating test was carried out at 80° C. The absorbance of the dimer of 2,8-dimethylpyrido[3,2-g]quinoline of the present invention was not changed even under the heating condition of 80° C., 20 days. This result was same as that of the dimer of pyrido[2,3-g]quinoline shown in FIG. 1.

In addition, when this same was irradiated by mercury lamp at 254 nm after the heating test, the dimer was restored to original 2,8-dimethylpyrido[3,2-g]quinoline accompanied by the reversion of the absorbance to the position before irradiation at 365 nm.

EXAMPLE 5

(2,8-di-tert-butylpyrido [3,2-g]quinoline)

To 4,6-diaminoisophthalaldehyde (0.82 g) which was prepared in the same manner as Example 3, 3,3-dimethylbutane-2-on (20 g) was added and the temperature elevated to 90°-100° C. To this system, 10% potassium hydroxide/ethyl alcohol solution (2.0 ml) was added and stirred for 3 hours.

After the end of the reaction, the reaction mixture was concentrated to ⅓ to yeld crystal readily.

Elemental Analysis: Calculated: C: 82.06, H: 8.28, N: 9.66. Found: C: 82.17, H: 8.15, N: 9.68.

After 2,8-di-tert-butylpyrido [3,2-g]quinoline (3 mg) from above process was dissolved in cyclohexanol (20 g) and determined its absorbance by spectrophotometer, it was irradiated by UV-radiation from a spectroirradiator at a wavelength near 365 nm for 10 minutes. After the change of the absorbance was recorded, a heating test was carried out at 80° C. The absorbance of the dimer of 2,8-di-tert-butylpyrido[3,2-g]quinoline of the present invention was not changed even under the heating condition of 80° C., 20 days. This result was same as that of the dimer of pyrido[2,3-g]quinoline shown in FIG. 1.

In addition, when this sample was irradiated by a mercury lamp at 254 nm after heating test, the dimer was restored to the original 2,8-di-tert-butylpyrido [3,2-g]quinoline accompanied by the reversion of the absorbance to the position before irradiation at 365 nm.

EXAMPLE 6

(Pyrido[3,2-g]quinoline-2,8-dicarboxylic acid)

After pyrido[3,2-g]quinoline-2,8-dicarboxylic acid (3 mg) prepared in the same manner as Example 3 was dissolved in ethylene glycol (20 g) and its absorbance determined by spectrophotometer, it was irradiated by UV-radiation from a spectroirradiator at a wavelength near 365 nm for 10 minutes. After the change in absorbance was recorded, a heating test was carried out at 80°. The absorbance of the dimer of pyrido[3,2-g]quinoline-2,8-dicarboxylic acid of the present invention was not changed even under the heating condition of 80° C., 20 days. This result was same as that of the dimer of pyrido[2,3-g] quinoline showed in FIG. 1.

In addition, when this sample was irradiated by mercury lamp at 254 nm after the heating test, the dimer was restored to the original pyrido [3,2-g]quinoline-2,8-dicarboxylic acid accompanied by the reversion of the absorbance to the position before irradiation at 365 nm.

The Elemental Analysis of the pyrido[3,2-g]quinoline-2,8-dicarboxylic acid was as follows:

Elemental Analysis: Calculated: C: 62.62, H: 3.01, N: 10.53, O: 23.84. Found: C: 62.57, H: 3.11, N: 10.43, O: 23.89.

EXAMPLE 7

(Dimethyl pyrido [3,2-g]quinoline-2,8-dicarboxylate)

Dried methyl alcohol (15 cc) was added to pyrido[3,2-g]quinoline-2,3-dicarboxylic acide (0.536 g) to make solution under nitrogen atmosphere. To this solution cooled at 0° C., 100% sulfuric acid (2.5 cc) was added dropwise and refluxed for 3 hours. After the end of the reaction, added ice water (50 cc) and neutralized with potassium hydrogen carbonate solution. The reaction mixture was extracted with dichloromethane four times. The extract was dried on sodium sulfate and evaporated solvent to yield yellow crystal.

Elemental Analysis: Calculated: C: 64.80, H: 4.09, N: 9.54, O: 21.58. Found: C: 64.72, H: 4.18, N: 9.55, O: 21.35.

After dimethyl pyrido[3,2-g]quinoline-2,8-dicarboxylate (3 mg) from the above process was dissolved in butyl alcohol (20 g) and its absorbance determined by spectrophotometer, it was irradiated by UV-radiation from a spectroirradiator at a wavelength near 365 nm for 10 minutes. After the change in absorbance was recorded, a heating test was carried out at 80° C. The absorbance of the dimer of dimethyl pyrido[3,2-g]quinoline-2,8-dicarboxylate of the present invention was not changed even under the heating condition of 80° C., 20 days. This result was same as that of the dimer of pyrido [2,3-g]quinoline shown in FIG. 1.

In addition, when this sample was irradiated by mercury lamp at 254 nm after heating test, the dimer was restored to original dimethyl pyrido[3,2-g]quinoline-2,8-dicarboxylate accompanied by reversion of the absorbance to the position before irradiation at 365 nm.

Therefore, according to the present invention, there is provided an organic photochromic compound comprising the compound which is selected from pyrido[3,4-g]isoquinoline, pyrido[2,3-g]quinoline, pyrido[3,2-g]quinoline or pyrido[3,2-g]quinoline derivatives.

Namely, with respect to these special heterocyclic compounds, the dimerization reaction of the compounds may occur reversibly by photoirradiation at a wavelength near 354 nm and 254 nm, and said dimers do not change even under the heating condition for 20 days at 80° C.

Since this reversible photoresponsivity may be employed conveniently to recording and rewriting and the recording condition is maintained stably, these compounds are organic photochromic compounds with excellent properties with respect to long term preservability and thermal stability, and may be utilized for various recording-memory material, photosensitizer for rader, display material and the like.

What is claimed is:

1. An organic photochromic compound selected from the group consisting of a dimer of pyrido[3,4-g]isoquinoline of chemical formula

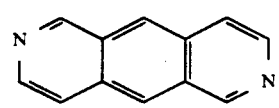

a dimer of pyrido[2,3-g]quinoline of chemical formula

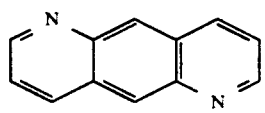

a dimer of pyrido[3,2-g]quinoline of chemical formula and

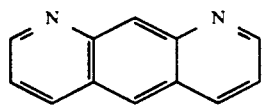

a dimer of pyrido[3,2-g]quinoline derivatives of chemical formula

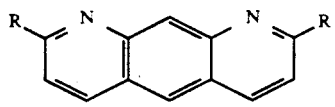

wherein R is methyl, ethyl, propyl, butyl, carboxy, carboxymethyl, or {carboxyethyl} carboxyethyl, wherein the dimer of each compound [I], [II], [III], and [IV] is formed by exposure of the compound [I], [II], [III], and [IV], respectively, to light of wavelength 320 to 400 nm, and wherein the dimers of [I], [II], [III], and [IV] can be reconverted to the compounds [I], [II], [III], and [IV], respectively, by exposure to light of wavelength 230 to 300 nm.

* * * * *

UNITED STATES PATENT AND TRADEMARK OFFICE
CERTIFICATE OF CORRECTION

PATENT NO. : 5,091,535
DATED : February 25, 1992
INVENTOR(S) : Shigeru Nomura and Takashiro Hidaka It is certified that error appears in the above-identified patent and that said Letters Patent is hereby corrected as shown below:

Col. 4, line 40, please delete the second formula and the ",";

Col. 14, line 10, after "formula" insert --[I]--;

Col. 14, line 18, after "formula" insert --[II]--;

Col. 14, line 26, after "formula" insert --[III]--;

Col. 14, line 36, after "formula" insert --[IV]--;

Col. 14, line 44, please delete "{carboxyethyl}".

Signed and Sealed this

Twenty-fourth Day of August, 1993

Attest:

BRUCE LEHMAN

*Attesting Officer*     *Commissioner of Patents and Trademarks*